(12) United States Patent  
Scherrible et al.

(10) Patent No.: US 9,416,472 B2
(45) Date of Patent: Aug. 16, 2016

(54) METHOD FOR THE PRODUCTION OF A BODY IMPLANT

(71) Applicant: Admedes Schuessler GmbH, Pforzheim (DE)

(72) Inventors: Frank Scherrible, Pforzheim (DE); Florent Budillon, Pforzheim (DE)

(73) Assignee: ADMEDES SCHUESSLER GMBH (DE)

( * ) Notice: Subject to any disclaimer, the term of this patent is extended or adjusted under 35 U.S.C. 154(b) by 316 days.

(21) Appl. No.: 13/969,065

(22) Filed: Aug. 16, 2013

(65) Prior Publication Data

US 2014/0035183 A1 Feb. 6, 2014

(30) Foreign Application Priority Data

Aug. 16, 2002 (DE) .................. 10 2012 016 301

(51) Int. Cl.
| | |
|---|---|
| *D04C 1/06* | (2006.01) |
| *A61F 2/90* | (2013.01) |
| *A61F 2/06* | (2013.01) |
| *A61F 2/82* | (2013.01) |
| *A61F 2/07* | (2013.01) |

(52) U.S. Cl.
CPC ... *D04C 1/06* (2013.01); *A61F 2/06* (2013.01); *A61F 2/07* (2013.01); *A61F 2/82* (2013.01); *A61F 2/90* (2013.01); *A61F 2002/072* (2013.01); *A61F 2250/0031* (2013.01); *D10B 2509/06* (2013.01)

(58) Field of Classification Search
None
See application file for complete search history.

(56) References Cited

U.S. PATENT DOCUMENTS

| | | | |
|---|---|---|---|
| 8,177,834 | B2 | 5/2012 | Carlson et al. |
| 2009/0099643 | A1 | 4/2009 | Hyodoh et al. |

*Primary Examiner* — Benjamin Schiffman
(74) *Attorney, Agent, or Firm* — Gerald E. Hespos; Michael J. Porco; Matthew T. Hespos

(57) ABSTRACT

A method for production of a body implant (1), having the steps: generating a braiding (10) from a first fiber material (12); executing a first heat treatment on the braiding (10); removing part of the fibers of the first fiber material (12), and replacing by a second fiber material (14) or reinsertion of the first fiber material (12) after the execution of a further processing step on the removal part of the fibers of the first fiber material (12).

20 Claims, 10 Drawing Sheets

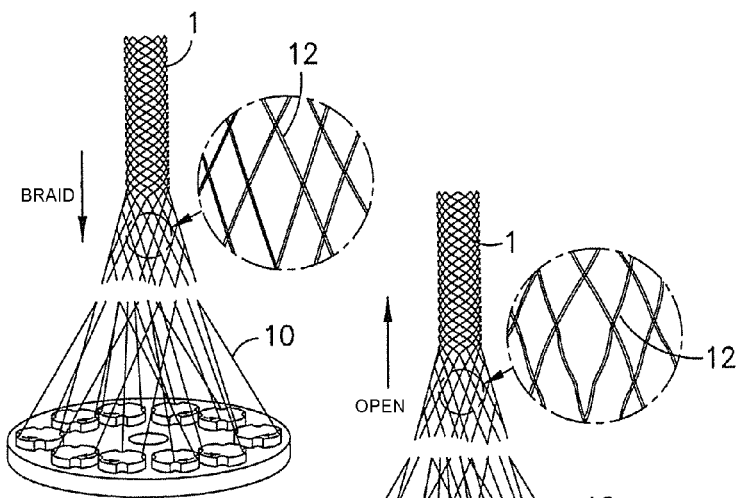
FIG.1a
FIG.1b
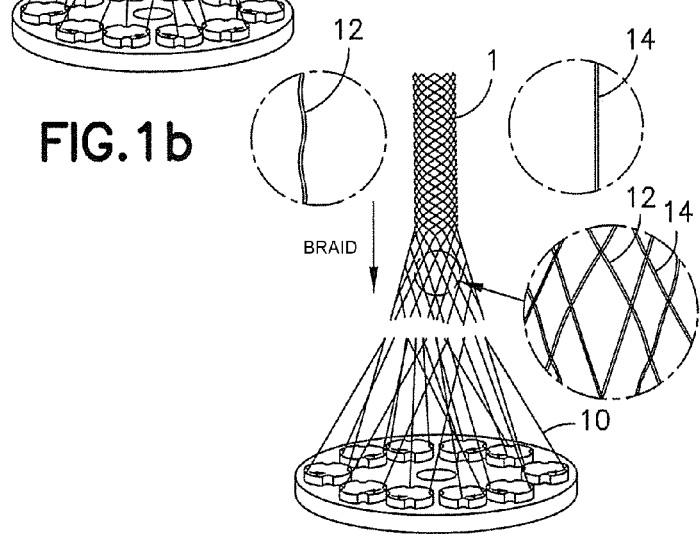
FIG.1c

METHOD FOR THE PRODUCTION OF A BODY IMPLANT

BACKGROUND OF THE INVENTION

1. Field of the Invention

The present invention relates to a method for the production of a body implant and to a body implant, such as, for example, a stent, a vascular aid, a stent graft, a cardiac valve frame, an occluder, a flow diverter or the like.

2. Description of the Related Art

Body implants of this type are produced, for example, by the generation of textile structures from a material. It is difficult in this case to combine the material of the textile structure with other materials, as would be desirable, for example, for the introduction of markers in the form of a yarn or wire for the purpose of increasing X-ray visibility or the like. Furthermore, at least one of the materials should be given shape memory properties, for example by means of what is known as a shape setting step.

DE 696 24 834 T2 discloses a method for the production of a vascular prosthesis composed of metallic and nonmetallic yarns.

According to the prior art, it was not possible, with a combination of metallic and nonmetallic yarns, to carry out heat treatment for shape setting, as it is known. The prior art therefore had to rely, for shaping, on shaping by plastic deformation. Reference is made in this respect to the publications DE 696 24 834 T2 and DE 603 13 735 T2.

However, shaping based on heat treatment is to be preferred to shaping based on plastic deformation, since plastic deformation entails the risk of material damage. It was recognized that components in which shape setting ideally takes place as a result of a heat treatment of at least metallic yarns have different mechanical properties from what is the case with plastically deformed yarns.

In body implants, for example, the fatigue behavior may be adversely influenced by plastically deformed yarns.

The object of the present invention, therefore, is to make it possible to have a connection of at least two different materials or material properties within a textile structure of, for example, a body implant.

SUMMARY OF THE INVENTION

According to one aspect, a method for production of a body implant, includes the steps of generating a textile structure or a braiding from a first fiber material or wire or yarn; executing a first shaping on the textile structure or the braiding, for example by a heat treatment; removing part of the fibers of the first fiber material, and replacing by a second fiber material or wire or yarn or reinserting the first fiber material after the execution of a further processing step on the removed part of the fibers of the first fiber material.

By removing part of the fibers or of the wires or of the yarn on the finished textile structure or the finished braiding, this part can be replaced by a second different fiber material having different properties. Alternatively or additionally, the first fiber material can also be reused after the execution of a further processing step, such as, for example, electro polishing and/or coating. The removal of part of the fibers of the first material may take place, for example, by reverse braiding, for example by the braiding machine being operated in the opposite direction, in order to remove part of the fibers already incorporated into the braiding from the braiding again.

Preferably, the step "replacing by a second fiber material or wire or yarn or reinserting the first fiber material after the execution of a further processing step on the removed part of the fibers of the first fiber material" is followed by a step of the (re)generating of the textile structure or of a (new) textile structure.

According to a further aspect, a method for the production of a body implant includes the following steps of generating a (first) textile structure or of a braiding from a first fiber material or wire or yarn; executing a first shaping on the (first) textile structure of the braiding, for example by a heat treatment; opening the (first) textile structure out of the first fiber material; providing at least one second fiber material; and producing a (second, modified) textile structure from the first fiber material, combined with the at least second fiber material.

The term "opening" is to be understood, in particular, to mean that the braiding is debraided again. An "opening" may be understood to mean a reversal or inverse operation for generating a textile structure or of a braiding. For example, a textile structure/braiding may be opened by reverse braiding.

Preferably, during opening, the first fiber material is "held in position". For example, ends of the first fiber material can (still) remain fixed by means of holding devices, such as grippers or wire, so that only the previous braiding operation, to be precise the generating of the first textile structure/braiding, is reversed or canceled. Furthermore, a second fiber material or further fiber materials can then be "added", so that a (new, second, modified) textile structure can then be generated which comprises both first fiber material and second and, if appropriate, further fiber material.

In addition, in a step, parts/fibers of the first fiber material can be removed before or after an opening of the (first) textile structure.

According to the above methods, after the incorporation of the second fiber material, the textile structure can be subjected to a second shaping or heat treatment which is configured such that, during the second shaping, only the second fiber material acquires shaping (shape setting). This is achieved, for example, in that a second heat treatment is carried out at a lower temperature and/or with a shorter period of action than the first heat treatment. The second heat treatment thus leads to a shaping of the second fiber material, without the shaping executed on the first fiber material during the first heat treatment being influenced. Should it not be possible not to influence the shaping of the first fiber material by carrying out the second heat treatment, for example when the temperatures of the first and the second heat treatment are too close to one another, the second heat treatment on the second fiber material may also take place separately before the insertion of the second fiber material into the textile structure.

The method may further have the step of executing a second shaping or heat treatment on the second fiber material, the second shaping or heat treatment being configured such that only the second fiber material acquires shaping.

Preferably, a second heat treatment is carried out at a lower temperature than the first heat treatment.

In this case, the heat treatment serves for shaping the textile structure or the braiding. The fiber material subjected to textile processing is, for example, heated for a stipulated period of time in order to execute a shaping step. In this case, for example, stresses in the fiber material which have arisen as a result of textile processing are reduced or essentially eliminated.

A further example may be a shape memory effect, such as many materials, inter alia nitinol, possess. This means that, initially, there is in what is known as a martensite structure a metal microstructure which is converted into an austenite structure by phase transition as a result of an increase in the temperature. What is unusual in the case of nitinol is that this transition is reversible, without plastic defects occurring. Phase transition takes place without diffusion, that is to say without the atoms changing their places in the lattice structure.

In particular, during this diffusion-free reversible phase transition of the austenite structure to the martensite structure, the atoms assume an ordered twinning arrangement by straightforward shear deformation.

The second shaping or heat treatment preferably is executed on the textile structure generated from the two fiber materials or is executed separately before the insertion of the second fiber material.

The textile structure preferably is generated by textile processing, braiding, weaving or knitting.

The textile structure or the braiding may have at least one third fiber material.

Preferably, at least one of the fiber materials is electro polished and/or coated before final incorporation into the textile structure or the braiding. This step can also take place after the removal of part of the first fiber material. In other words, first, a textile structure is generated, then a first shaping step by a first heat treatment is executed, and, after the removal of part of the fibers of the first fiber material, this part of the first fiber material is electro polished and/or coated and is subsequently incorporated into the textile structure again.

The first fiber material may have nitinol and the second or the third fiber material may have one of a polymer, of a biodegradable polymer and of tungsten. Nitinol is suitable, in particular, for the generation of shape memory properties, for example in order to expand a compressed body implant, such as, for example, a stent, after placement in the body by virtue of the shape memory properties. Tungsten can, for example, increase the X-ray visibility of a body implant.

At least one of the fiber materials may have shape memory properties.

According to the above methods, fiber material may comprise, in particular, one or more fibers and/or one or more wires and/or one or more yarns. In other words, a first fiber material may be formed from one or more fibers. Additionally or alternatively, a first fiber material may be formed from one or more yarns. Additionally or alternatively, a first fiber material may be formed from one or more wires. The same likewise applies accordingly to second, third, fourth, etc. fiber material.

Advantageously, the second and/or further fiber material may serve as an auxiliary material, for example in order to achieve higher impermeability. In particular, more than two fiber materials may be combined. For example, a third or a fourth fiber material may also be combined or interlaced in addition to a second fiber material. In other words, further fiber materials may be combined with the first and the second fiber material, in which case the fiber materials may have properties (strength, toughness, rigidity, bioresorbability, etc.) which are different from one another.

The above mentioned methods enable, a textile structure to be produced that has a shape combination in that two or more textile structures are connected to one another. It is possible in this case to combine different materials, but also identical materials, by means of identical or different preceding processing steps. The term "different preceding processing steps" is to be understood, for example, to mean that the fiber materials are/have been subjected to different thermal treatments. For example, a first and a second fiber material may be produced from the same material, such as, for example, nitinol, but the first fiber material may be/have been subjected to another heat treatment different from that of the second fiber material.

In a further refinement, the first fiber material may comprise different materials or treatments. For example, the first fiber material may comprise polymer threads/yarns and nitinol threads/wires. A second fiber material which is combined with the first fiber material has in this case preferably other material-induced and/or treatment-induced properties.

Advantageously, the above methods allow the flexible configuration of textile structures. Inter alia, according to the above methods, a subsequently incorporated fiber material can leave a (main) structure in order to provide or to form a dedicated follow-up structure. For example, a textile structure can be formed by the combination of the first and the second fiber material, (only) the second fiber material being led out of this textile structure or being led further on, in order to form a dedicated textile structure/follow-up structure. Furthermore, for example, (only) a third fiber material may be led out of the (main) textile structure in order to form a follow-up structure, while the first and the second fiber material are not led further on in the follow-up structure.

The method enables production of filter components or comparable components having an outer rigid structure for anchoring to the vessel and having a more flexible inner part.

The first fiber material preferably is a heat-treatable metal or a heat-treatable nonmetal.

Preferably, the second fiber material is composed of metal and/or nonmetal. The third fiber material or further fiber material also preferably is composed of metal of nonmetal.

The second fiber material is composed of coated yarn or coated wire. Preferably, furthermore, the third and, if appropriate, further fiber materials are composed of coated yarn or coated wire. Preferably, the second and the further fiber material or fiber materials may have different yarns or wires and/or coatings.

Preferably, the second and the further fiber material or fiber materials may have different yarns/wires and/or coatings.

The first fiber materials may remain in the textile structure and an at least second fiber material is introduced.

The second fiber material may be composed of the same material as the first fiber material, with the second fiber material having been subjected to a shaping different from that of the first fiber material. The same also applies similarly to third, fourth, etc. fiber material.

The second fiber material preferably comprises a second material different from that of the first fiber material. In addition, the second fiber material preferably is subjected to shaping different from that of the first fiber material. The same also applies similarly to third, fourth, etc. fiber material.

The second fiber material preferably comprises the same material as the first fiber material, although the second fiber material has properties different from those of the first fiber material and/or has been processed differently. For example, the first fiber material and the second fiber material may be/have been treated with heat treatments different from one another, such as, for example, an austenite finish (AF). Furthermore, the first and the second fiber material may have coatings different from one another, such as gilding, PTFE coating, etc. The same also applies similarly to third, fourth, etc. fiber material.

The second and/or further fiber material may be introduced/inserted as a connecting element or connecting material between two textile structures. The same also applies similarly to third, fourth, etc. fiber material. In other words, the second fiber material and/or a third, fourth, etc. fiber material may form a connecting element between at least two textile structures.

The invention also relates to a body implant in the form of a textile structure. The body implant comprises a material combination with a shape memory material and/or a superelastic material. For example, the body implant may have nitinol or phynox in combination with another fiber material or with an identical fiber material, but with different properties, in which the imprinted shape of at least the first material is achieved via a heat treatment.

The invention also relates to a body implant, such as, for example, a stent, a stent graft, a vascular aid, a cardiac valve frame or the like, the body implant having a textile structure or a braiding composed of a first fiber material or of a second fiber material, a first heat treatment for generating a shaping (shape setting) being carried out at least on the first fiber material.

Preferably, the body implant has at least two different fiber materials. For example, one fiber material may be nitinol with shape memory properties and the other fiber material may be a material with good X-ray visibility, such as, for example, tantalum or gold.

The body implant may also have a third and further different fiber materials. These may have polymers, biodegradable polymers, tungsten or the like.

Preferably, one of the above body implants is a vascular prosthesis.

Preferably, one of the above body implants is a stent graft.

Preferably, one of the above body implants is an occluder.

Preferably, one of the above body implants is a flow diverter.

Preferably, one of the above body implants is an aneurysm coil.

Preferably, one of the above body implants is a cardiac valve frame.

Preferably, one of the above body implants is an abdominal aortic aneurysm (AAA) stent.

Preferably, one of the above body implants is a thoracic aortal aneurysm (TAA) stent.

Preferably, one of the above body implants is a gastroenterological stent.

Preferably, one of the above body implants is a peripheral stent.

The invention, then, is explained in more detail by means of the accompanying drawings and preferred exemplary embodiments.

BRIEF DESCRIPTION OF THE DRAWINGS

FIG. 1 shows, in step a), the generating of a braiding with a first fiber material and, in step b), the shape setting after the execution of the first heat treatment on the braiding and also, in step c), the replacement of part of the first fiber material by a second fiber material.

DETAILED DESCRIPTION OF THE PREFERRED EMBODIMENTS

Figure 2:
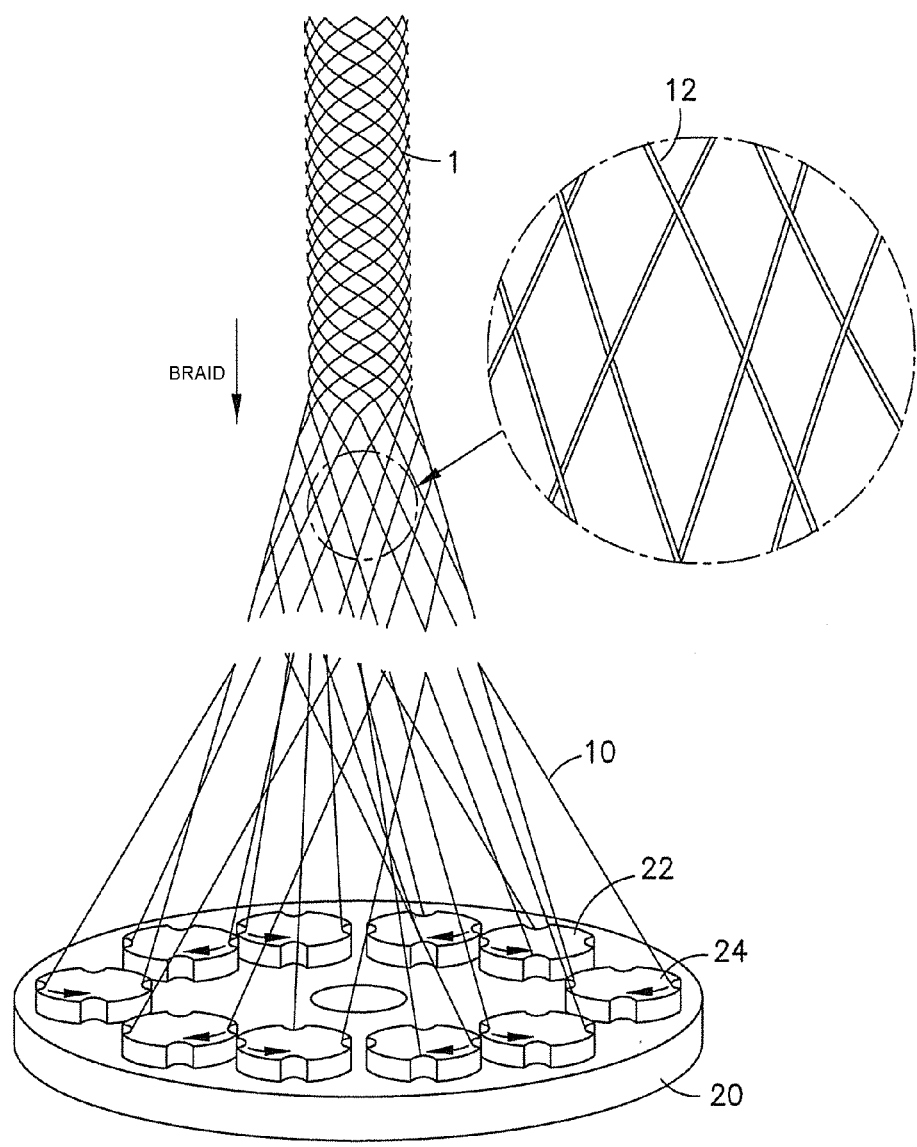
FIG. 2 shows the generating of a braiding with the first fiber material by means of a braiding machine.

As shown in FIG. 1a and FIG. 2, according to a preferred exemplary embodiment, a braiding is first generated as a textile structure 10 with a first fiber material 12 by means of a braiding machine 20 which has first bobbins 22 and second bobbins 24. For this purpose, the first bobbins 22 rotate counterclockwise and the second bobbins 24 rotate clockwise. A body implant 1 in a tubular configuration can be generated from the textile structure 10 or the braiding.

Figure 3:
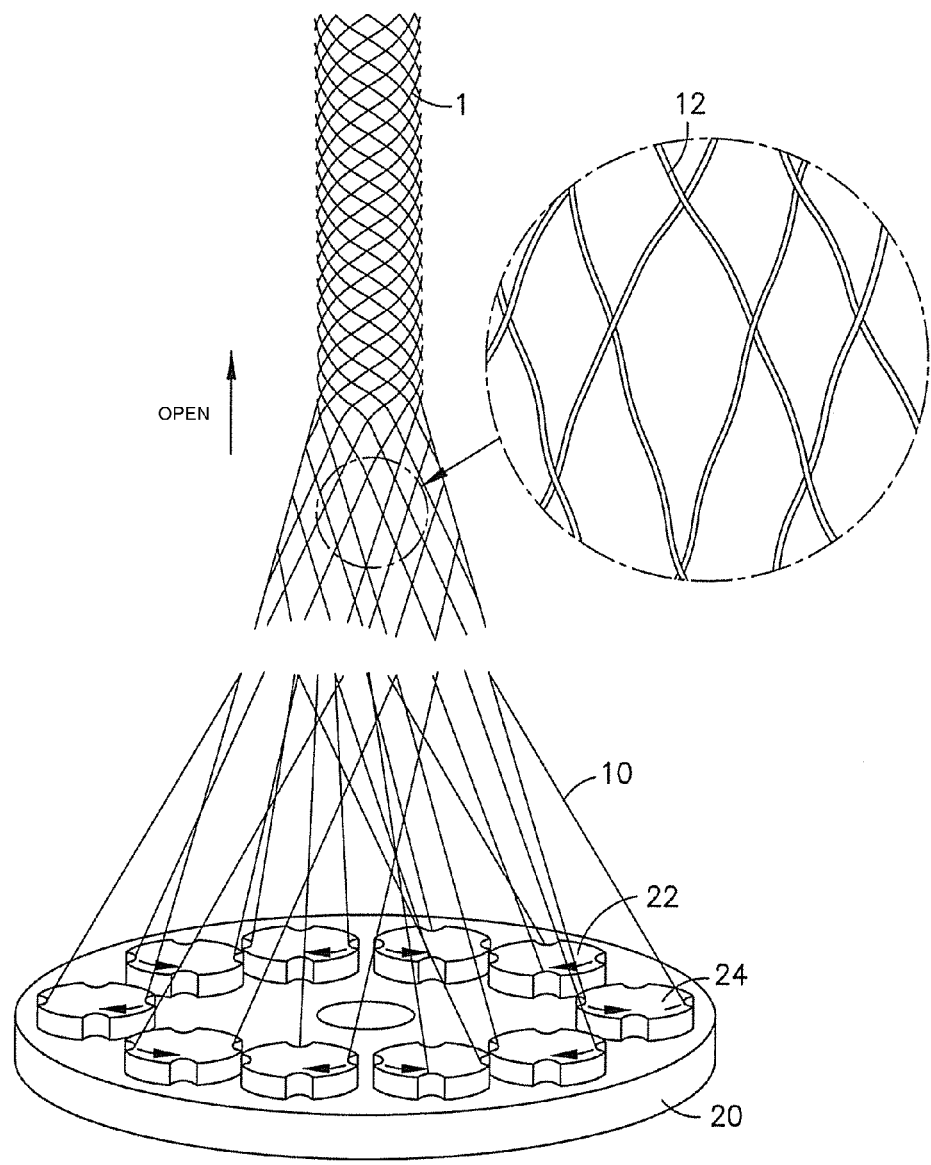
FIG. 3 shows the running in reverse of a braiding machine for the removal of part of the first fiber material on which a heat treatment for the shaping was previously carried out.

As shown in FIG. 3, a first heat treatment for generating a shaping of the first fiber material 12 is carried out on the textile structure 10 or the braiding. The first fiber material 12, for example nitinol, thereby acquires a shaping with shape memory properties, for example in order to cause expansion after the insertion of the body implant 1 into a living body.

In this case, the heat treatment serves for shaping the braiding 10. The first fiber material 12 subjected to textile processing is, for example, heated for a stipulated period of time, in order to execute a shaping step. In this case, for example, stresses in the first fiber material 12 which have arisen as a result of textile processing are reduced or essentially eliminated.

The further example may be a shape memory effect, such as many materials, inter alia nitinol, possess. This means that, initially, in what is known as a martensite structure in the first fiber material 12 there is a metal microstructure which is converted into an austenite structure by phase transition as a result of an increase in the temperature. What is unusual in the case of nitinol is that this transition is reversible, without plastic defects occurring. Phase transition thus takes place without diffusion, that is to say without atoms changing their places in the lattice structure.

In particular, during this diffusion-free reversible phase transition of the austenite structure into the martensite structure, the atoms assume an ordered twinning arrangement as a result of a straightforward shear deformation.

Figure 4:
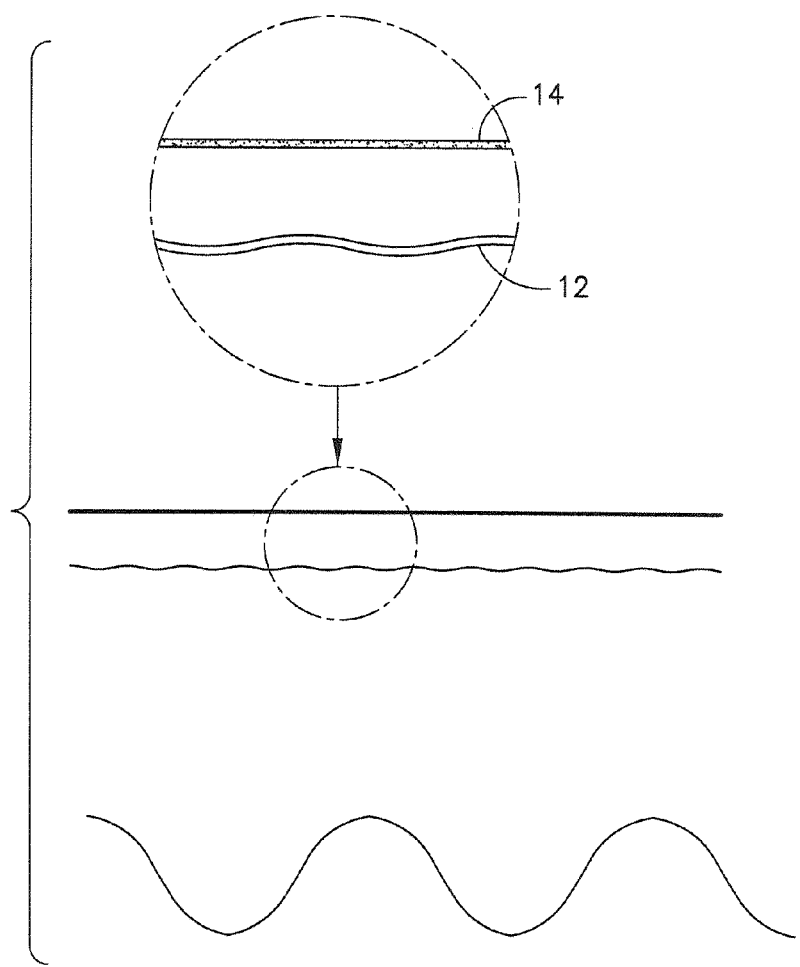
FIG. 4 shows individual fibers of a first and of a second fiber material, a shaping having been executed on the first fiber material.

FIG. 4 shows the first fiber material 12 with shaping executed by means of the first heat treatment step and also a second fiber material 14 which has not yet undergone heat treatment. Accordingly, the first fiber material 12 has, for example, a wave-like shape, while the second fiber material 14 has a straight wire or yarn shape.

As shown in FIG. 3, after the shaping step, part of the first fiber material 12 can be removed from the braiding 10 in that the braiding machine 12 is operated in reverse, that is to say the first bobbins 22, which rotate counterclockwise in normal operation, then rotate clockwise, and the second bobbins 24, which rotate clockwise in normal operation, are then rotated counterclockwise. In this way, the finished braiding 10 composed of the first fiber material 12 having undergone the shaping step is partially opened.

The first fiber material 12 can then be introduced into the partially opened braiding 10 again after the executing of a further treatment step, for example, as a further treatment step, the first fiber material 12 can be electro polished or coated at intersections.

This is not possible or is possible only under difficult conditions within the braiding 10. By part of the first fiber material 12 being removed, this can be electro polished and/or coated separately from the braiding 10, in order to have high quality. The part of the first fiber materials 12 is then incorporated into the braiding 10 again by braiding.

The further treatment step may also involve what is known as drug eluting, that is to say coating with a medication, in that the first fiber material 12 is, for example, dipped into a solution of the medication or sprayed with this. After introduction to a human body, the medication thus applied to the body implant 1 can be dispensed successively there.

For example, what is known as a drug eluting stent (DES) as a body implant 1 can release small quantities of drugs which inhibit cell reformation. Two active substances have proved successful in treatment with medication-releasing stents: the immunosuppressive sirolimus and the cancer therapeutic paclitaxel. Such stents may be used, for example, for the therapy of coronary heart disease.

Alternatively, instead of the removed part of the first fiber material 12 or of part thereof, a second fiber material 14 with different properties may also be incorporated. For example, when the first fiber material 12 has nitinol, the second fiber material may have a polymer, a biodegradably polymer and/or tungsten.

Figure 5:
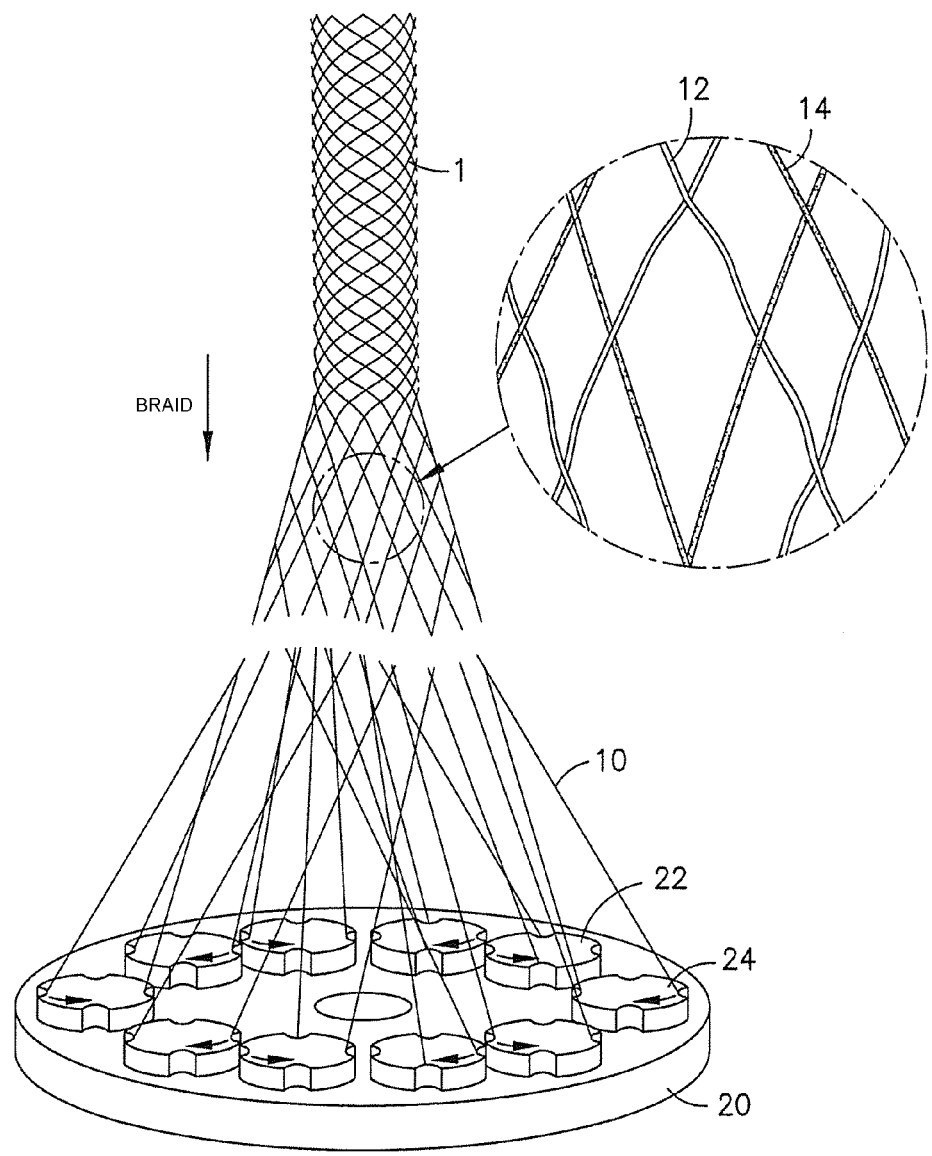
FIG. 5 shows the replacement of the removed part of the first fiber material by a second fiber material.
Figure 6A:
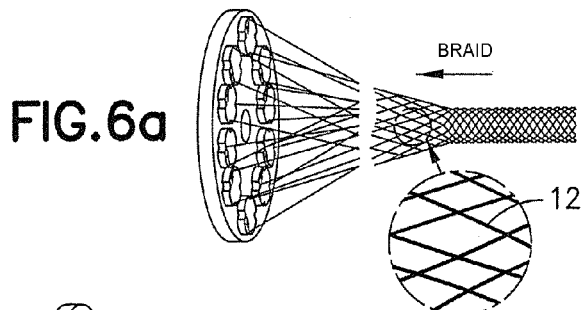
FIG. 6 shows, in step a), the generating of a braiding with a first fiber material and, in step b), the executing of a first heat treatment on the braiding composed of the first fiber material.
FIG. 6d) shows the generating of a braiding with a second fiber material and FIG. 6c) shows the executing of a second heat treatment on the braiding composed of the second fiber material.
FIG. 6e) shows the bringing together of the first and of the second fiber material in a braiding.
Figure 6B:
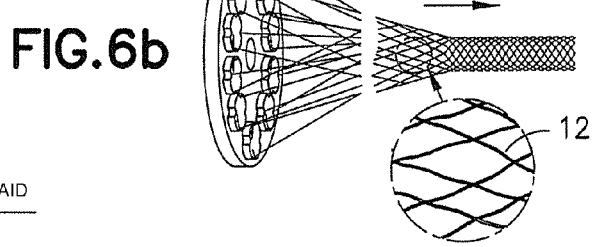
Figure 6E:
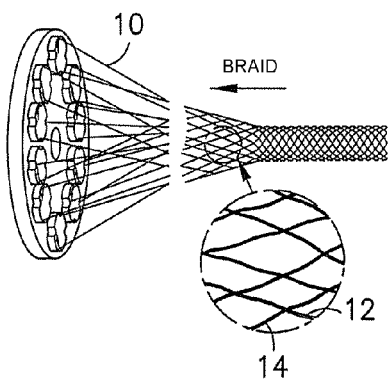
Figure 6C:
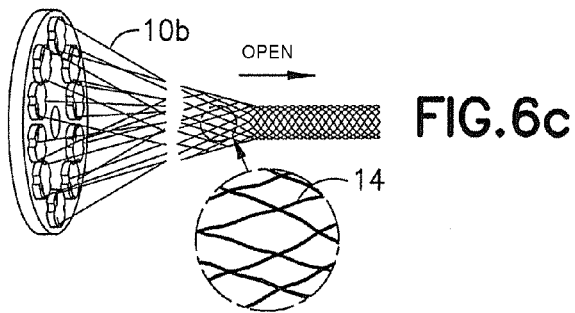
Figure 6D:
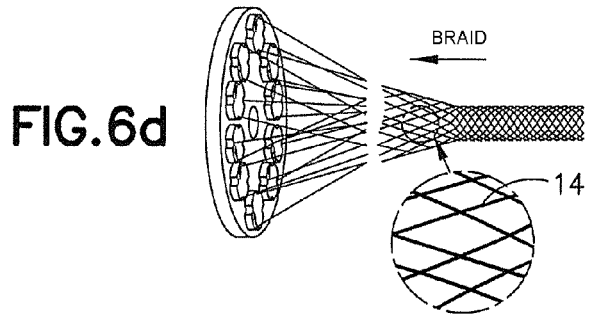

After the incorporation of the second fiber material 14, the braiding 10 has both fibers composed of the first fiber material 12 and the fibers composed of the second fiber material 14, as shown in FIG. 5.

Subsequently, on the finished braiding 10 composed of the first fiber material 12, with the already executed shaping, and of the second fiber material 14 without shaping, a second shaping step can be executed by carrying out a second heat treatment on the finished braiding 10. In this case, the second heat treatment should be configured such that the shaping of the first fiber material 12 is essentially uninfluenced. This is achieved, in particular, in that the second heat treatment is carried out at a lower temperature than the first heat treatment and/or for a shorter period of time than the first heat treatment.

Should the temperatures of the first and the second heat treatment of the first and the second fiber material 12, be too close to one another, so that an undesirable influencing of the shaping of the first fiber material 12 by the second heat treatment cannot be avoided, the heat treatments may also be carried out separately, as shown in FIG. 6. In this method, a braiding 10*a* is generated from the first fiber material 12, as shown in step a), and a first heat treatment is carried out on the first fiber material 12, as shown in step b). The same takes place separately with the second fiber material 14, that is to say a braiding 10*b* is generated from the second fiber material 14, as shown in step d), and a second heat treatment is carried out on the braiding 10*b* generated from the second fiber material 14, as shown in step c).

The two braidings 10*a*, 10*b* are then brought together into a braiding 10, as shown in step e) of FIG. 6. This may take place, for example, in that one of the previously generated braidings 10*a*, 10*b* from steps a, b or c, d is completely opened or disentangled and is braided into the other braiding 10*b*, 10*a* in each case, or part of one braiding 10*a* is removed and this part is replaced by the fiber material 14 of the other braiding 10*b*.

Figure 7A:
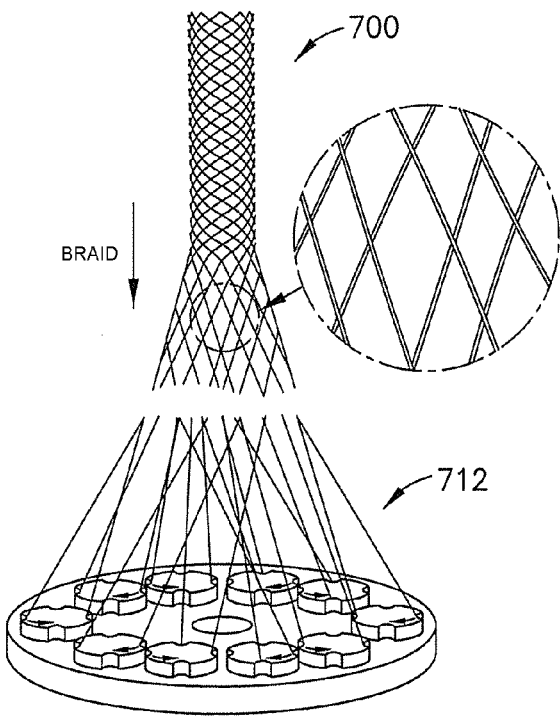
FIG. 7 shows diagrammatically the producing of a textile structure from a first fiber material, combined with at least one second fiber material.
Figure 7B:
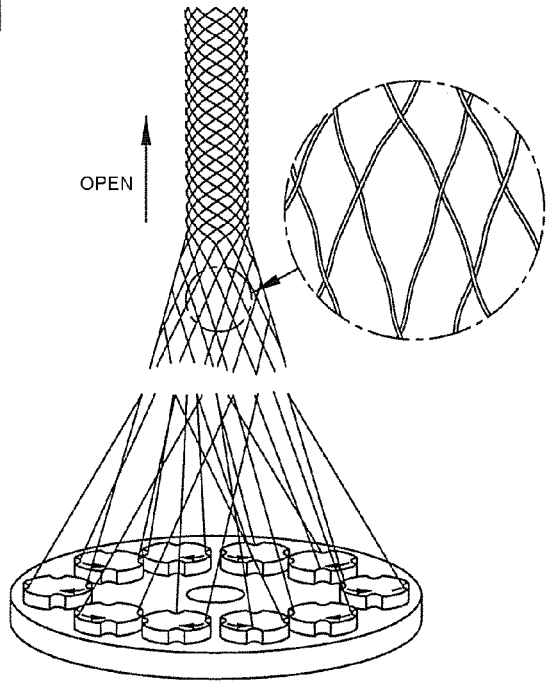
Figure 7C:
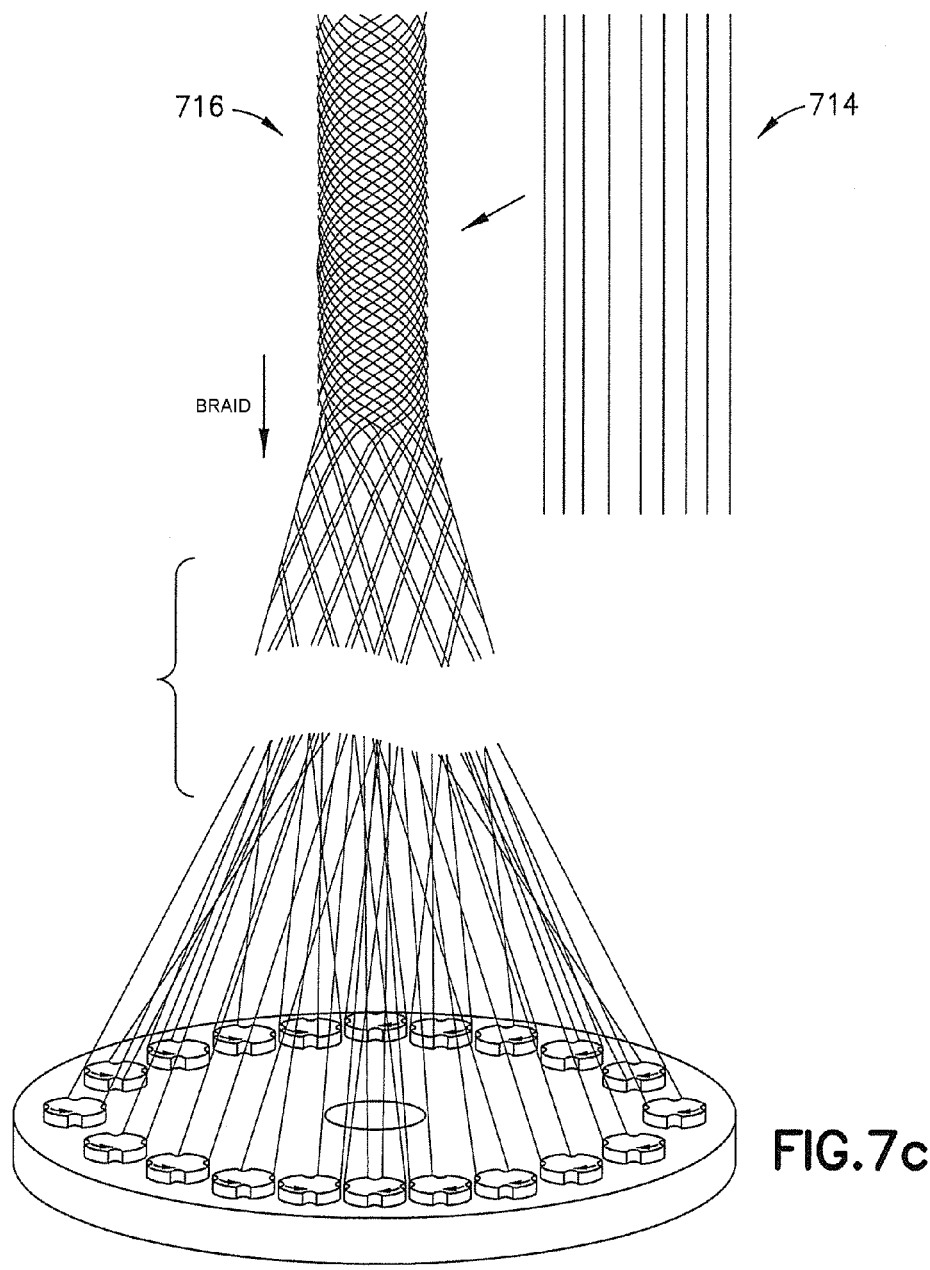

FIG. 7 shows diagrammatically the producing of a textile structure from a first fiber material, combined with at least one second fiber material. In particular, FIG. 7 shows, in step a), the generating of a textile structure 700 or of a braiding 700 from a first fiber material 712 and, in step b), the executing of first shaping on the textile structure or the braiding, for example by a heat treatment, and also, in step c), the producing of a modified textile structure 716 from the first fiber material 712, combined with the at least second fiber material 714.

Figure 8:
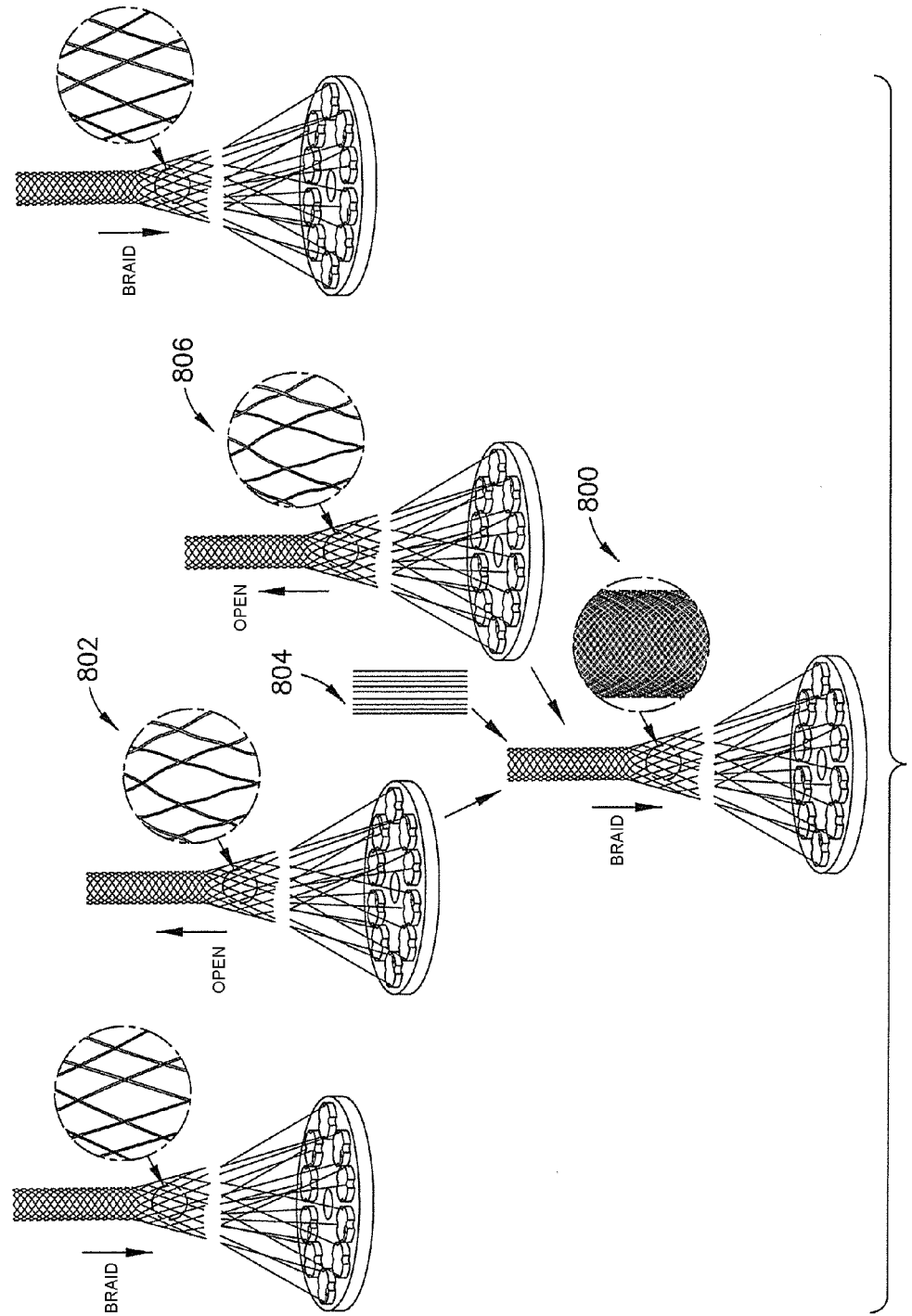
FIG. 8 shows a basic diagram of a textile structure with a shape combination in that two or more textile structures are connected to one another.

FIG. 8 shows a basic diagram of a textile structure with a shape combination 800, in that two or more textile structures are connected to one another.

In particular, FIG. 8 shows a first textile structure 802 which is connected to a second textile structure 804. The second textile structure 804 is connected in turn to a third textile structure 806. These three textile structures connected to one another or merging one into the other form the shape combination 800.

Figure 9A:
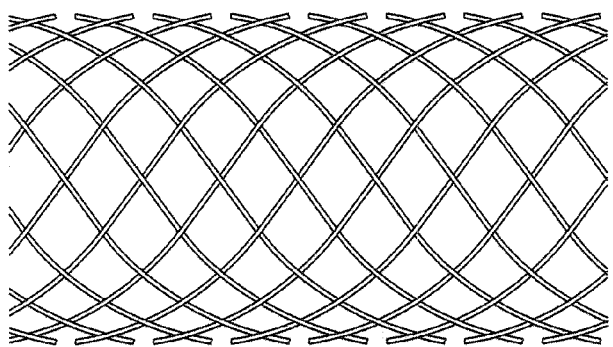
FIG. 9 shows a basic diagram of a textile structure in which the second fiber material leaves the original textile structure and forms a dedicated structure/shape.
Figure 9B:
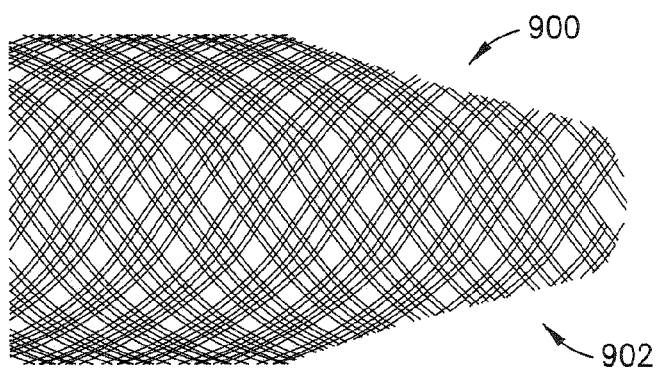
Figure 9C:
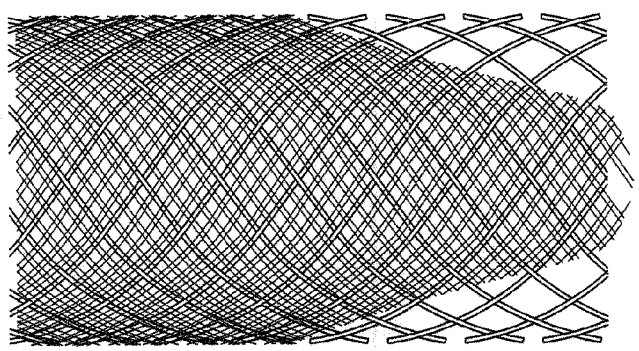

FIG. 9 shows a basic diagram of a textile structure in which the second fiber material leaves the original textile structure and forms a dedicated structure/shape.

As is clear from FIG. 9, textile structures of flexible configuration can be provided. FIG. 9 shows a fiber material which is subsequently incorporated into a main structure 900 and leaves the main structure 900 in order to provide or to form a dedicated follow-up structure 902. For example, a textile structure can be formed by the combination of the first and the second fiber material, (only) the second fiber material being led out of this textile structure or being lead further on, in order to form a dedicated textile structure/follow-up structure. For example, the main structure 900 may correspond to a textile structure 716, the follow-up structure being produced in a further production step, for example braiding.

As explained above, by means of the novel method, a braiding 10 for generating a body implant 1, such as, for example, a cardiac valve, a stent or a vascular aid, can be generated, which is composed of two different fiber materials 12, 14. Furthermore, at least one third material (not shown) can also be braided into the braiding 10 of the body implant 1. In this case, different heat treatments can be carried out on the different fiber materials 12, 14 in order to generate a shaping (shape setting). The braiding 10 can thereby acquire stipulated shape memory properties and at the same time have advantageous properties, for example, with regard to biocompatibility, biodegradability or X-ray visibility. For example, markers made from an X-ray-visible material can advantageously be incorporated into the braiding 10.

The invention is not restricted to braiding, but instead the textile structure 10 may also be generated by a textile processing, weaving or knitting. The fiber material 12, 14 may also be a wire or a yarn. Furthermore, the invention is not restricted to the execution on a braiding machine 20, but may also be implemented by any other textile processing machine which can generate a corresponding textile structure. The method is not necessarily restricted to body implants, but may also be extended to all areas of application in which it is necessary to implement a textile structure with two materials which must be heat-treated (at least one material), but cannot be heat-treated simultaneously.

Advantageously, blood flow through a vessel can be improved by a body implant formed according to the invention when it is inserted into the vessel. Introduced fibers can, inter alia, influence the flow behavior. This is utilized, for example, in what are known as flow diverters in which the blood stream is deflected and, for example, cuts off an aneurysm from the blood stream.

If multifilaments are used, the surface is markedly increased. It may prove advantageous to increase thrombogenity for the formation of occlusions, for example occluders for LAA (Left Atrial Appendage) or PFO (Patent Foramen Ovale).

With a suitable surface property, the formation of epithelial cells could be promoted. If a degradable material is used, the remaining metallic material can be reduced to a minimum. This could have a positive effect upon the number of reocclusions, what is known as restenosis.

Furthermore, a body implant according to the invention can be more easily deformable and, in particular, expandable in a vessel.

What is claimed is:

1. A method for production of a body implant (1), comprising the steps:
    generating a textile structure (10), from at least one first fiber material (12);
    executing a first shaping on the textile structure (10);
    removing part of the fibers of the first fiber material (12), and
    replacing by a second fiber material (14) and/or reinserting of the first fiber material (12) after the execution of a further processing step on the removed part of the fibers of the first fiber material (12).

2. The method of claim 1, further having the step of executing a second shaping on the second fiber material (14, 714), the second shaping being configured such that only the second fiber material (14, 714) requires shaping.

3. The method of claim 2, wherein the second shaping is executed at a lower temperature than the first shaping.

4. The method of claim 2, wherein the second shaping is executed on the textile structure (10, 716) generated from the first and second fiber materials (12, 712; 14, 714) or is executed separately before the inserting the second fiber material (14, 714).

5. The method of claim 1, wherein the textile structure (10, 700, 716) is generated by textile processing, braiding, weaving or knitting.

6. The method of claim 1, wherein the textile structure (10, 716) has at least one third fiber material.

7. The method of claim 6, wherein:
    the first fiber material (12, 712) is connected partially to the second fiber material (14, 714) and/or to the third fiber material, and
    the second fiber material (14; 714) and/or the third fiber material, after leaving a main structure (900), form a dedicated follow-up structure (902).

8. The method of claim 1, wherein at least one of the fiber materials (12, 712; 14, 714) is electro polished or coated before final incorporating into the textile structure (10, 716).

9. The method of claim 1, wherein the first fiber material (12, 712) has nitinol and the second (14, 714) has one of a polymer, a biodegradable polymer and of tungsten.

10. The method of claim 1, wherein at least one of the fiber materials (12, 712; 14, 714) has shaped memory properties.

11. The method of claim 1, wherein the first fiber material (12, 712) is a heat-treatable metal or a heat-treatable non-metal.

12. The method of claim 1, wherein the second fiber material (14, 714) fiber material is composed of metal and/or nonmetal and/or of coated yarn.

13. The method of claim 1, wherein the second fiber material (14, 714) has the same material as the first fiber material (12, 712), and the second fiber material (14, 714) has been subjected to a shaping different from that of the first fiber material (12, 714) and/or has different properties and/or has been processed differently.

14. The method of claim 1, wherein the second fiber material (14, 714) has a second material different from that of the first fiber material (12, 712), and the second fiber material (14, 714) is subjected to a shaping different from that of the first fiber material (12, 712).

15. The method of claim 1, wherein the second fiber material (14, 714) forms a connecting element between at least two textile structures (802, 804, 806).

16. A method for production of a body implant, comprising:
    performing steps for generating a textile structure (700) or a braiding from a first fiber material (712);
    executing a first shaping on the textile structure (700) or the braiding;
    reversing at least one of the steps performed for generating the textile structure (700) or the braiding out of the first fiber material (712) to produce a partly deconstructed textile structure or a partly deconstructed braiding made from the first fiber material (712);
    providing at least one second fiber material (714); and
    producing a modified textile structure (716) made from the partly deconstructed textile structure or the partly deconstructed braiding combined with the at least one second fiber material (714).

17. The method of claim 16, wherein the step of executing a first shaping on the textile structure (700) or the braiding is carried out by heat treatment.

18. The method of claim 16, further comprising a step of executing a second shaping on the second fiber material (14, 714), the second shaping being configured such that only the second fiber material (14, 714) requires shaping.

19. The method of claim 18, wherein the second shaping is executed at a lower temperature than the first shaping.

20. The method of claim 18, wherein the second shaping is executed on the textile structure (10, 716) generated from the first and second fiber materials (12, 712; 14, 714) or is executed separately before the inserting of a second fiber material (14, 714).

* * * * *